(12) United States Patent
Arabia et al.

(10) Patent No.: US 6,569,079 B2
(45) Date of Patent: May 27, 2003

(54) VENTRICULAR ASSIST DEVICE, ACCESSORY THEREFORE AND METHOD OF USE

(75) Inventors: Maurizio Arabia, Rome (IT); Mauro Ercolani, Grottaferrata (IT); Manlio Fierli, Pontegaleria (IT); Stefano Rinaldi, Parma (IT); Giorgio Sorcini, Rome (IT); Maurizio Zagara, Rome (IT)

(73) Assignee: Ministero dell'Universita e della Ricerca Scientifica e Tecnologica, Rome (IT)

( * ) Notice: Subject to any disclaimer, the term of this patent is extended or adjusted under 35 U.S.C. 154(b) by 52 days.

(21) Appl. No.: 09/844,000

(22) Filed: Apr. 27, 2001

(65) Prior Publication Data

US 2002/0019577 A1 Feb. 14, 2002

(30) Foreign Application Priority Data

Apr. 28, 2000 (EP) .............................................. 00830321

(51) Int. Cl.$^7$ .............................................. A61N 1/362

(52) U.S. Cl. ....................................................... 600/16

(58) Field of Search .............................. 600/16, 17, 18; 623/3.1, 3.11, 3.16, 3.17

(56) References Cited

U.S. PATENT DOCUMENTS

| 3,860,968 | A |   | 1/1975  | Shapiro |         |
|-----------|---|---|---------|---------|---------|
| 4,152,786 | A | * | 5/1979  | Clark et al. | 138/30 |
| 4,731,076 | A |   | 3/1988  | Noon et al. |     |
| 4,759,760 | A |   | 7/1988  | Snapp, Jr. |      |
| 5,513,956 | A | * | 5/1996  | Lewis et al. | 417/12 |
| 5,957,137 | A | * | 9/1999  | Dalke et al. | 128/898 |
| 6,001,056 | A | * | 12/1999 | Jassawalla et al. | 600/16 |

FOREIGN PATENT DOCUMENTS

| DE | 2322103 | 11/1974 |
| DE | 3844375 | 7/1990  |
| EP | 659444  | 6/1995  |
| EP | 728488  | 8/1996  |
| FR | 1503906 | 2/1968  |
| FR | 2131144 | 11/1972 |
| WO | 9740865 | 11/1997 |

OTHER PUBLICATIONS

US 5,006,107, 4/1991, Robinson et al. (withdrawn)

Unger F, Deutsch M, Enenkel H, Fasching W, Losert U, Polzer K, Stellwag F, Thoma H, Wolner E, and Navratil J, *The Windkesselventricle with Guiding Balloon as a New Approach For Assisted Circulation* from Med Instrum; Sep.–Oct. 1976.

Matthias Loebe, MD, PhD, Johannes Muller, MD and Roland Hetzer MD, PhD, *Ventricular Assistance for Recovery of Cardiac Failure* from Current Opinion in Cardiology 1999, pp. 234–248.

Roland Hetzer, MD, PhD, Johannes Muller, MD, Yuguo Weng, MD, Gerd Wallukat, PhD, Susanne Spiegelsberger, MD, and Matthias Loebe, MD, PhD, *Cardiac Recovery in Dilated Cardiomyopathy by Unloading With a Left Ventricular Assist Device* from The Society of Thoracic Surgeons 1999; pp. 742–749.

(List continued on next page.)

*Primary Examiner*—Mahmoud Gimie
(74) *Attorney, Agent, or Firm*—Dorsey & Whitney LLP

(57) ABSTRACT

A device comprises a bag with associated actuator means which can be selectively activated to permit the expansion of the bag and its consequent filing with a body of blood which flows towards the bag, and to produce the contraction of the bag with the consequent expulsion from the bag of a body of blood which has flowed into the bag. Means are provided for selectively varying the resistance offered by the said bag to filing with the said body of blood.

19 Claims, 2 Drawing Sheets

OTHER PUBLICATIONS

O.H. Frazier, MD and Timothy J. Myers, BS, *Left Ventricular Assist System as a Bridge to Myocardial Recovery* from the Society of Thoracic Surgeons 1999; pp. 734–741.

J. Mueller, Y. Weng, M. Dandel, T. Drews, H. Bieda, M. Loebe and R. Hetzer, *Long–Term Results of Weaning From LVAD–It Does Work* from Deutsches Herzzentrum Berlin.

F. Miyawaki and T. Tsuji , *Recovery–Directed Left Ventricular Assist Device (RDLVAD)* from the National Cardiovascular Center Research Institute.

F. Miyawaki, T. Tsuji and Y. Fukui , *Recovery–Directed Left Ventricular Assist Device (RDLVAD) May Promote Cardiac Recovery* from National Cardiovascular Centre Research Institute, Tokyo Denki University, Japan in The International Journal of Artificial Organs, vol. 22, No. 6, 1999.

M. Zietkiewicz, B. Perek, B Meyns, G. Dispersyn, L. Messoten, L. Mortelmans, M. Borgers and W. Flameng, *Potential for Recovery in Animal Model of Chronic Heart Failure* from the International Journal of Artificial Organs, vol. 22, No. 6, 1999.

*Texas Heart Institute Uses Thoratec VAD System as Bridge to Recovery for Patient—Eliminating Need for Heart Transplant* from Thoratec Laboratories' Newsletter, vol. 14, Issue 2, Jun. 1999.

Konstantina Dipla, PhD, Julian A. Mattiello, BA, Valluvan Jeevanandam, MD, Steven R. Houser, PhD and Kenneth B. Margulies, MD, *Myocyte Recovery After Mechanical Circulatory Support in Humans With End–Stage Heart Failure* from the American Heart Association, Inc. 1998.

Tofy Mussivand, PhD, Paul J. Hendry, MD, Roy G. Masters, MD, Kevin S. Holmes and Wilbert J. Keon, MD, *Circulatory Support Devices for Bridge to Recovery* from The Society of Thoracic Surgeons, 1998.

Eric A. Rose, MD and O.H. Frazier, MD, *Resurrection After Mechanical Circulatory Support* from Circulation, vol. 96 No. 2, Jul. 15, 1997.

*Thoratec Receives FDA Approval for Expanded Use of its Ventricular Assist Device (VAD) System* from Thoratec Laboratories' Newsletter, vol. 12 Issue 2, Jun. 1998.

\* cited by examiner

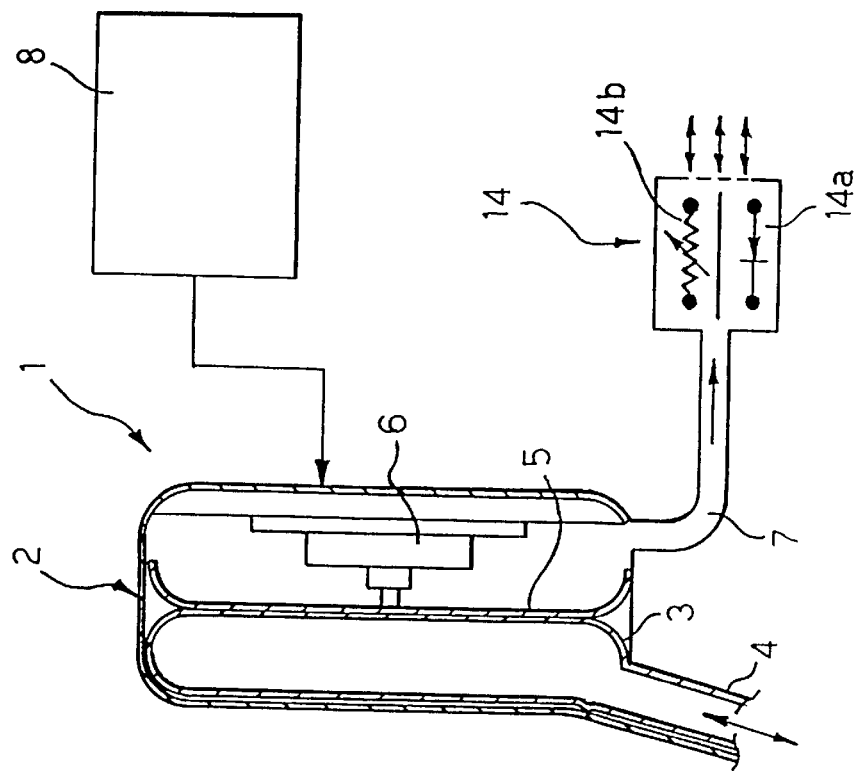
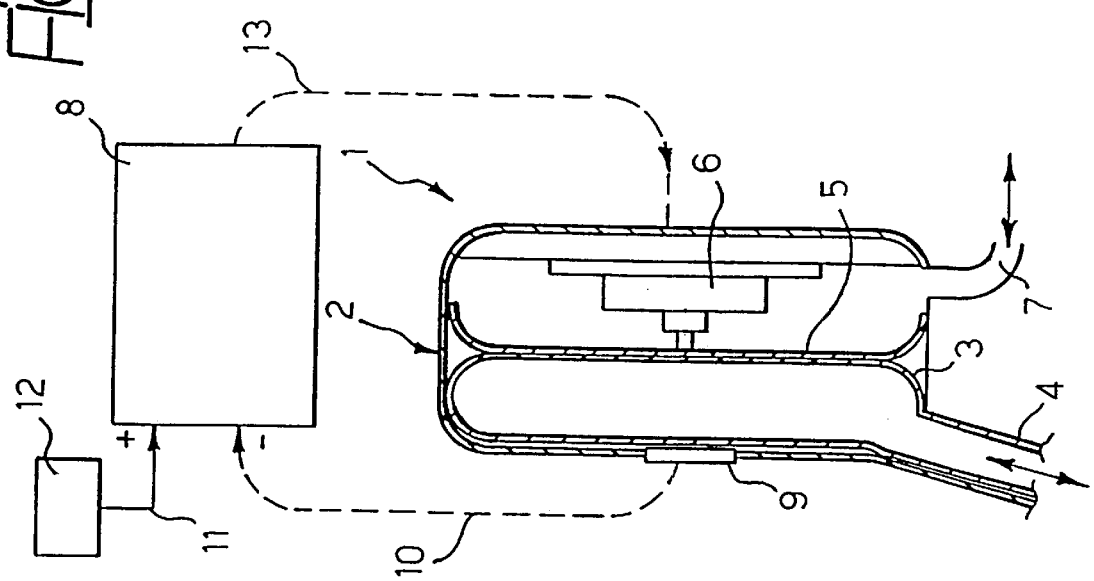

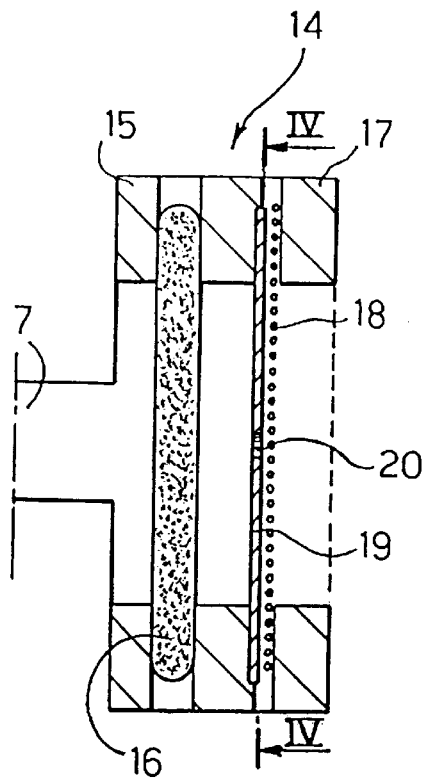
Fig_3
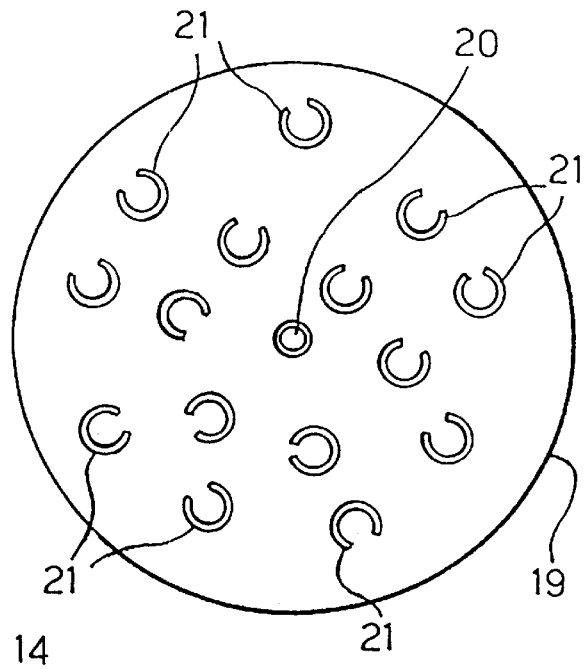
Fig_4
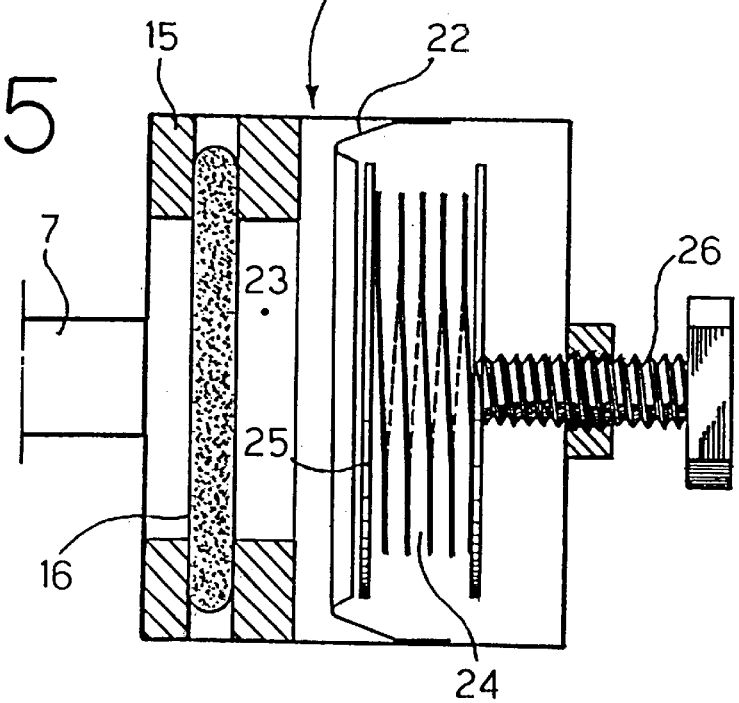
Fig_5

VENTRICULAR ASSIST DEVICE, ACCESSORY THEREFORE AND METHOD OF USE

BACKGROUND OF THE INVENTION

The present invention relates in a general way to devices for cardiac ventricular assistance, commonly known as VADs (an acronym for Ventricular Assist Device).

Devices of this kind (such as those described, for example, in EP-A-0 728 488 and EP-A-0 728 489) are designed to be used to assist a heart muscle by replacing the left ventricle which is no longer capable of carrying out an adequate action of pumping the blood to the circulatory system.

For this purpose, the device is connected in such a way as to act between the left atrium and the aorta, producing a connection arranged in fluid dynamic terms in parallel with the natural circuit, or—in a connection device which tends to be preferred—in a position interposed between the apical region of the left ventricle and the aorta, and therefore in series with the natural circuit.

Other systems of connection between the VAD and the cardiovascular system have been and can be proposed (for example what is known as the "Windkessel" system—F. Unger et al., Med. Instrum. 1976, vol. 10, p. 256), and could be reconsidered in the future.

The devices in question are at present mainly used as what is known as a bridge to transplantation, in other words as an aid designed to maintain circulatory function in a patient waiting for a heart transplant operation. However, they are also suitable for use in a form of long-term assistance and it is expected that this application may become widespread in the near future.

More recently, an application as what is known as a bridge to recovery has been assuming a degree of importance.

In this case, the ventricular assistance device is designed to be used for a limited period (for example 3–4 months), so that it temporarily replaces the left ventricle which in the meantime can recover, possibly as the result of suitable treatment, a level of function sufficient to enable the patient to return to substantially normal living conditions after the removal of the VAD.

This application is of the "therapeutic" type, in other words it would enable the patient to be cured and subsequently allow him to return to a substantially normal life (a good quality of life). On the other hand, the long-term use of a VAD (or a complete artificial heart) as a fixed prosthesis makes the patient completely and permanently dependent on the device and on the corresponding supply and control systems, with significant restrictions on his independence and quality of life.

The results obtained up to the present time are very promising; however, they have revealed the highly critical nature—for the purposes of achieving a truly satisfactory end result—of the method of controlling the VAD, in other words of the possibility or otherwise of synchronizing the action of the VAD with that of the natural heart, and of the management of what is known as the weaning phase, in other words the phase in which, after having been totally replaced by the ventricular assistance device in its function, the recovering ventricle is gradually returned to the performance of its function, with the objective of achieving the removal of the ventricular assistance device when the ventricle has recovered a satisfactory level of function.

For example, the paper by M. Loebe et al., "Ventricular assistance for recovery of cardiac failure", published in Current Opinion in Cardiology, 1999, 14:234–248, describes a weaning method which essentially proposes the operation of the ventricular assistance device at a fixed frequency and gradually reducing this frequency as the weaning proceeds. The main drawback of this solution is that the frequency of intervention of the device, being fixed, and therefore generally different from that of the natural heart, can give rise to situations in which the ventricular assistance device comes to carry out its pumping action in opposition to the pumping action which is beginning to be carried out again by the natural ventricle. In these conditions, the natural ventricle is subjected to a high fluid dynamic load: in practice, the natural ventricle can be in systole and attempt to pump the blood located within it while the ventricular assistance device is also in systole. Although accidental, this event can have a rather negative effect on the execution of the weaning phase, and may even prevent its success.

The paper by F. Miyawaki et al., "Recovery-Directed Left Ventricular Assist Device (RDLVAD) May Promote Cardiac Recovery", presented at the XIIth ISAO/XXVIth ESAO Joint Congress at Edinburgh, Aug. 3–6, 1999, describes a ventricular assistance device consisting of a valved apical duct, a ventricular load control chamber of the yielding type, and a pump. The device allow the natural ventricle to eject the blood into the aforesaid chamber, whose degree of yield can be selectively adjusted. It is thus possible to produce fluid dynamic loads for the natural heart which are adjustable, and which may be considerably lower than the load corresponding to the aortic pressure in the recovery phase and gradually increase in the weaning phase; the function of pumping blood from the aforesaid yielding chamber to the aorta continues to be carried out by the pump of the device.

Regardless of any other consideration, this solution has the drawback of requiring the presence of at least one additional element (the bag or chamber with adjustable yieldingness) which has to be designed to be located—and therefore implanted—in a position interposed between the apex of the heart and the VAD.

SUMMARY OF THE INVENTION

The object of the present invention is to provide a solution which can enable a weaning stage to be carried out according to principles which, on the one hand, are optimal in terms of the recovery of the function of the natural ventricle, and, on the other hand, make it unnecessary to implant elements additional to the elements forming the cardiac ventricular assistance device.

According to the present invention, this object is achieved by means of a device having the characteristics claimed in a specific way in the following claims.

The invention also relates to an accessory, considered as an independent element, capable of being coupled to a ventricular assistance device for the application of the solution according to the invention, and also to the corresponding procedure for using the device.

The invention will now be described, purely by way of example and without restrictive intent, with reference to the attached drawings, in which:

BRIEF DESCRIPTION OF THE DRAWINGS

FIG. 1 shows schematically the structure of a ventricular assistance device according to a first embodiment of the invention;

FIG. 2 shows another possible embodiment of the invention which is preferred at the present time;

FIG. 3 shows an accessory which can be used in the application of the invention according to the principles shown in FIG. 2;

FIG. 4 is essentially a view according to the line IV—IV in FIG. 3, and

FIG. 5 shows a further possible embodiment of the set of parts shown in FIG. 3.

DETAILED DESCRIPTION OF THE INVENTION

In the attached drawings, the reference 1 indicates as a whole a ventricular assistance device (VAD) made, for example, according to the principles illustrated in EP-A-0 728 488 and EP-A-0 728 489. For this reason, in the remainder of the present description the characteristics of this device will be mentioned in a summary way, attention being focused on the characteristic elements of the solution according to the invention.

For this purpose it will be sufficient to note that the device 1 essentially comprises a casing 2 (made from biocompatible material, for example titanium) which can be implanted in a region of the thorax or abdomen.

Inside the casing 2 there is a deformable bag 3 provided with corresponding ducts for the admission and emission of blood, indicated jointly by 4.

As can be inferred from the description of the two European patent applications cited above (to which reference should be made for the illustration of the corresponding details of application), there are usually two ducts 4, one designed to act as a duct for the admission or inflow of blood into the bag 3 and the other designed to act as the duct for the emission or outflow of blood from the bag 3.

In the typical implantation condition, the two ducts 4 are connected, through corresponding tubes, in one case to a blood collection orifice formed (usually in the apical position) in the left ventricle of the user, and in the other case to the aorta of the user.

The ducts have corresponding associated valves (usually consisting of cardiac valves of the prosthetic type, for example of the tilting disc type), designed to impart to the ducts the necessary characteristics of unidirectionality in respect of the flow of blood from the left ventricle to the bag 3 and from the bag 3 to the aorta.

This connection enables the bag 3 to replace the user's left ventricle in the execution of the operation of pumping the blood to the aorta, and therefore towards the circulatory system.

For this purpose, the device 1 comprises an actuator designed to enable the bag 3 to do the following, in alternation:

expand, to receive the blood from the user's left ventricle, and contract, to expel the blood collected in the bag 3 towards the aorta.

The valves mentioned above are designed to ensure that:

on the one hand, the inflow of the blood from the user's ventricle to the VAD bag is not countered by the opposing pressure of the blood present in the aorta (and in the circulatory system located downstream of the aorta in fluid dynamic terms), and on the other hand, the pressure developed within the bag 3 when it contracts to pump the blood to the aorta is not propagated back towards the user's left ventricle.

In the example of embodiment illustrated (which, it should be remembered, is only an example), the aforesaid alternating movement of expansion and contraction of the bag 3 is produced by means of an actuator of the electromechanical type, essentially comprising a plate 5 which can selectively compress (in practice, flatten) the bag 3 against an opposite wall of the casing 2, and an electric motor 6 which can act on the plate 5 by means of a telescopic screw.

As stated previously, the structure of the device 1 mentioned here by way of example matches that described in the European patent applications cited a number of times above, making it unnecessary to provide a more detailed description in this document.

The alternating movement of expansion and contraction of the bag 3 can also be produced in a different way, for example by means of fluid actuators, or electrical actuators different from those described above, and possibly by making use of elastic means such as springs subjected to an opposing action by actuators.

As will be more clearly appreciated from the following text, the solution according to the invention lends itself to being applied in ventricular assistance devices of the most varied type, and therefore largely independently of the nature and operating principles of the actuator elements used, and of the specific geometric, mechanical and constructional characteristics of the bag 3.

The numeric reference 7 shows a further duct (normally leading to a transcutaneous line when the device 1 is implanted into the patient's body), which has the function of permitting the inflow and outflow of air to and from the inner volume of the casing 2 of the device. This takes place, in particular, from and to a volume external to the patient's body (for example the external atmosphere). The aforesaid inflow/outflow is clearly induced by the variations of volume to which the bag 3 is subjected as a result of the alternating movement of expansion and contraction produced by the actuator 5, 6.

The operation of the device 1, and particularly the operation of the motor 6, is controlled by an electronic control device 8 whose characteristics are to be considered as being fully known from the prior art and from the current activities of the applicant.

In particular, there are various known principles for synchronizing the operation of the motor 6 with the user's heartbeat.

The synchronizing action can be of the positive type, being produced, for example, in accordance with an electrocardiograph signal.

According to the solution preferred by the applicant at present, the synchronization is achieved by causing the motor 6 to be operated, on completion of the contraction phase of the bag 3 corresponding to the ejection of blood to the aorta, by the circuit 8 in such a way that it causes a rapid return of the plate 5 to the condition (withdrawn to the right with respect to the viewpoint in FIGS. 1 and 2) in which the bag 3 is left free to expand under the action of the blood which flows in from the user's heart.

In these conditions, the bag 3 offers minimum resistance to the action of filling. At the same time, a sensor (for example a flow sensor located in the duct 4 through which the blood flows from the user's left ventricle into the bag 3) makes it possible to detect when this flow rate decreases as a result of the completion of the natural systole.

At this point, the circuit 8 acts on the motor 6, operating it again in the direction which causes the advance of the plate 5 and the consequent flattening of the bag 3, with consequent execution of the action of pumping the blood from the bag 3 towards the aorta. The whole operation continues until a return is made to the initial conditions described above, to permit a subsequent repetition of the cycle which has just been described.

The detection of the instants at which the filling of the bag 3 by the user's ventricle is completed makes it possible to generate a time base for synchronizing the operation of the device. The whole is done with the further possibility, in the presence of tachycardia for example, of making the frequency of intervention of the device 1 equal to half the frequency of the natural heartbeat: in this case, the filling of the bag 3 from the user's ventricle takes place as a result of two successive natural systoles—usually having a correspondingly reduced flow rate—to which the intervention of the device 1 is added in a successive moment to execute the action of pumping the blood into the aorta.

Essentially similar operating methods can be implemented by monitoring the inflow/outflow of the air through the duct 7 or by monitoring the force (or pressure) which the bag 3 exerts on the plate 5.

In the solution according to the invention, the bag 3 is made to be associated with means capable of selectively varying the resistance offered by the bag 3 to the action of filling by the blood from the user's ventricle, in other words of controlling the fluid dynamic load experienced by the natural heart.

Thus, starting from initial conditions such as those described above, in which this resistance has a minimum value, it is possible to intervene in the weaning phase in such a way as to gradually and selectively increase the resistance offered by the bag 3 to the filling action caused by the natural ventricle, while maintaining an operation of the VAD which is synchronized with the rhythm of the natural heart. All this is continued until, on completion of the weaning phase, conditions are reached in which the bag 3 loses virtually all of its characteristics of yieldingness, acting as a vessel through which the blood ejected by the user's left ventricle passes to the user's aorta, thus restoring the fluid dynamic conditions of the natural heart and circulatory system.

In the embodiment shown in FIG. 1, the aforesaid operating procedures are implemented by associating the bag 3 with a pressure sensor 9 (consisting, for example, of what is known as a strain gauge) which can generate on an output line 10 an electrical signal indicating the blood pressure present within the bag 3.

The circuit 8 is integrated with an additional feedback function (of a known type), which requires the presence of an input line 11 leading to a module 12 which can easily be integrated in the control panel of the circuit 8 or, simply, in one of the functions of the circuit 8, and possibly in a way relating to the external display. The module 12 can be used to selectively set a value or a time variation of the pressure corresponding to the value or time variation of the pressure which is to be maintained within the bag 3 during the phase of the filling of the bag 3 by the blood from the user's left ventricle.

According to a typical feedback control system, the circuit 8 acts on the motor 6 through the motor control line, indicated by 13, to regulate the movement of withdrawal of the plate 5 in such a way that the desired pressure level is maintained within the bag 3.

A person skilled in the art of automatic control systems will understand that—provided that the operating principle is retained—the described solution can be embodied in numerous variants which are functionally equivalent to that which has been described.

This is primarily true in respect of the pressure sensor 9, shown here as being located between the bag 3 and one of the walls of the casing 2 against which the bag 3 is pressed by the plate 5. The sensor 9 can, however, be located in a different position, for example by interposing it between the plate 5 and the bag 3, or by locating it in the duct 4 which connects the bag 3 to the user's ventricle. It is also possible to effectively integrate the sensor 9 into the control system of the motor 6: this is because, clearly, the mechanism for moving the plate 5 (and, consequently, the torque which the motor 6 must supply to cause the movement of the plate 5) is affected by the force which the bag 3 exerts on the plate 5.

In a further alternative embodiment, the pressure sensor 9 can effectively replace the flow sensor mentioned previously, which is designed to detect the completion of the phase of the filling of the bag 3 by the blood from the user's ventricle, and can consequently be used to control the frequency and phase of operation of the actuator.

By acting on the module 12, the person assisting the user during recovery of ventricular function can therefore provide a weaning strategy (effectively comparable to a real rehabilitation of the cardiac muscle for use) by gradually increasing the pressure level set within the bag 3 during its filling.

The whole is done with the possibility of:

maintaining in all cases (according to the principles described above) the synchronization of the operation of the device 1 with the movement of expansion and contraction of the user's heart, and intervening to reduce the resistance offered by the bag 3 to filling by the user's ventricle whenever it is found that the set level is too high for the degree of recovery of ventricular function which has currently been attained.

The diagram in FIG. 2 corresponds to the embodiment of the invention which is preferred at present.

In this embodiment, the structure of the device 1 is kept practically unchanged in respect of all the elements indicated by references 1 to 8. The action of selective modification of the resistance offered by the bag 3 to the filling action is carried out by operating on the vent line 7 by means of a control device 14 having the characteristics shown more clearly in FIG. 3. This device can easily be configured, wholly or in part, as a simple accessory (or, more correctly, as a set of accessories, according to the procedures described more fully below) which can be associated with a ventricular assistance device which, in its other aspects, retains its conventional characteristics.

Essentially, the device 14 can be envisaged as a kind of insert or plug which can be associated with the duct 7 in such a way that:

it permits in an essentially unimpeded way the inflow of air from the exterior to the interior of the casing 2 during the phase of contraction of the bag 3 (see the symbol of a diode 14a shown by way of schematic illustration in FIG. 2), and opposing with a selectively variable load the outflow of air from the interior of the casing 2 to the exterior (see the symbol of a variable resistance shown at 14b in the same FIG. 2).

In practice, the device 14 is designed to provide an action of selectively throttling the duct 7 in the direction of the outflow of the air to the exterior, in such a way that a certain resistance is offered to the movement of expansion of the bag 3.

Advantageously, the device 14 is configured in the form of an accessory comprising a kind of plug which can be associated with the termination 15 of the duct 7 located outside the user's body. Normally, the termination 15 is provided with a filter 16 (of a known type) designed to provide purification of the air in order to prevent the inflow of dust or possibly bacteria towards the casing 2.

In a particularly simple embodiment, the accessory 14 simply consists of a ring 17 which can be applied to the termination 15 and comprises a support grating 18 against which bears a diaphragm 19 having the characteristics shown more fully in FIG. 4.

This is a diaphragm of elastic material (for example silicone rubber) which has one or more orifices 20 of calibrated dimensions in a central position and is also provided with one or more strips 21 which can act as valve elements.

In particular, the diaphragm 19 is located (with respect to the grating 18) on the inner side of the device 14, in other words on the side facing the duct 7.

Consequently, the inflow of air from the exterior towards the duct 7 takes place (in a minimal way) through the orifice 20 and (in a maximal way, essentially without impediment) through the apertures disengaged by the strips 21 which are spread apart with respect to these apertures under the force of the air which flows with a very low pressure drop.

Conversely, the outflow of the air in the opposite direction (in other words from the duct 7 to the exterior) can take place only through the orifice or orifices 20: this is because the strips 21 are pushed by the air flowing out of the duct 7 against the grating 18, into a position in which they block the corresponding apertures.

The corresponding operating mechanism is known—as is its simplicity and reliability—from numerous applications, both of the industrial type (for example piston or membrane pumps) and in the sector of sports or leisure equipment (for example, pumps for inflating floating mattresses, small boats, rubber dinghies, etc.)

The level of resistance offered by the bag 3 to filling by the blood from the user's ventricle is therefore determined mainly by the dimensions and/or by the number of the orifice or orifices 20.

At the start of the weaning, it is therefore possible to use an accessory 14 provided with an orifice 20 or with a set of orifices with an overall net air passage cross section which is large (for example, only slightly less than the net dimensions of the duct 7), and then change gradually to accessories provided with orifices 20 having increasingly smaller numbers and/or dimensions, chosen preferably from a set of accessories 14 with characteristics predetermined selectively according to the progress of the weaning operation.

The solution described with reference to FIGS. 2 to 4 is suitable for embodiment in numerous variants, such as that shown in FIG. 5.

This consists in placing, at the end of the duct 7, the ring 15 and the filter 16 (which is essentially superfluous in this case), a flexible membrane 22 which closes the air compartment of the device, thus forming a deformable bag 23 whose elastance (understood as the ratio between the internal pressure and the volume) can be determined and varied, for example by means of a spring 24 which supports a plate 25 on which the membrane 22 bears. The intensity of the thrust action exerted on the plate 25 by the spring 24 can therefore be made adjustable by operation of the screw 26.

In particular, the accessory 14 shown in FIG. 5 can also be made to be removable from the duct 7, thus providing a number of possibilities including that of providing a set of accessories 14 comprising corresponding deformable bags 23 with different values of elastance (independently of the presence of the adjusting screw 26).

Other variant embodiments can readily be devised by a person skilled in the art on the basis of the present description: for example, it is possible to envisage a solution in which the orifice 20 of FIGS. 3 and 4 has a continuously variable resistance (cross section), or in which the device 14 is associated with one or more vent bags to which the duct 7 leads.

All the described solutions are shown to be particularly advantageous both because of their intrinsic simplicity and because of the fact that they enable the weaning operation to be conducted even by personnel not particularly skilled in the use of sophisticated types of control equipment (monitors, operating keyboards, etc.).

The various accessories 14 included in a set of the type described above, and characterized by different values of fluid dynamic resistance (in practice, by different net cross sections of the orifice or of the orifices 20 or by different values of elastance of the additional bag 23), can be made in different colours, so that they are easily identifiable in relation to the requirements for use even by personnel who are not particularly skilled.

Above all, if the patient shows difficulties due to the fact that the load imposed by the bag 3 is excessive for the level of recovery of ventricular function achieved at that time, it is possible, simply by removing the accessory 14, to return the device to the normal operating conditions corresponding to the minimum resistance to filling of the bag 3 and consequently maximum effectiveness of the ventricular assistance.

The accessory 14 of FIGS. 3 and 4 can if necessary also be made in such a way that it can be fitted on the termination 15 of the duct 7 in an arrangement which is exactly the opposite of that shown in the cited figures. In this case, the accessory 14 operates in such a way that it does not impede the outflow of air from the casing 2 to the external environment, but opposes the inflow of air from the external environment to the casing 2. This movement of inflow of air from the exterior is caused when the bag 3 contracts under the action of the motor 6. The action of the motor is a powerful action, effectively unimpeded by the resistance to the inflow of air through the duct 7 exerted by the accessory 14 (fitted "in reverse", as it could be expressed): the net result is that, at the end of the stroke in which the bag 3 is compressed by the plate 5, the pressure level created within the casing 2 is at least marginally lower (by an amount depending on various factors, but primarily on the dimensions and number of the orifices 20 provided in the accessory 14) than the level of atmospheric pressure. In these conditions, when the motor 6 reverses its direction of operation, withdrawing the plate 5 so that it disengages the bag 3, the aforesaid subatmospheric pressure level has the effect of promoting the expansion of the bag 3, in other words of promoting the inflow of blood from the user's ventricle to the bag 3.

In this case, the action of selective modification of the resistance to filling offered by the bag has what might be called a negative effect with respect to that described previously. In other words, when the accessory 14 is fitted "in reverse", the overall effect is to increase the level of assistance to ventricular function offered by the device 1 beyond the level offered in normal conditions of use. A fitting device of this kind can therefore be used, for example, in the period immediately following the implanting of the VAD, when, either because of the disease which has made it necessary to assist the natural heart, or, possibly, because the traumatic effect of surgery, the contractility of the natural heart is reduced to such an extent as to make it difficult for the bag 3 to be filled by the natural heart, possibly simply because of the small resistance to the flow of blood caused by the tube which connects the natural heart to the VAD, or where attacks might occur during the weaning. All this is done while maintaining the characteristics of extreme simplicity of use described above, and therefore permitting rapid and safe operation even by personnel not specifically trained in this field.

Clearly, provided that the principle of the invention is retained, the details of construction and the forms of embodiment can be varied widely from those described and illustrated without thereby departing from the scope of the present invention as defined by the attached claims.

What is claimed is:

1. A cardiac ventricular assistance device comprising:
   a bag selectively adapted for at least first expanding to permit the filling of the bag with at least some of a body of blood flowing towards the bag;
   the bag selectively adapted for at least second contracting to expel from the bag at least some of the body of blood which has flowed into the bag;
   means for selectively varying the resistance offered by the bag to filling with at least some of the body of blood;
   a containing casing enclosing the bag; and
   a duct leading to the containing casing, the duct permitting the inflow and outflow of a gaseous substance to and from the containing casing following the expansion and contraction of the bag; wherein:
   the means for selectively varying the resistance offered by the bag comprises:
      throttling means acting selectively on the duct in at least one of said inflow and outflow directions; and
      valve means permitting in an essentially unimpeded way flow of said gaseous substance in the other of said inflow and outflow directions.

2. A device of claim 1, wherein the throttling means are removably coupled to the duct.

3. The device of claim 1, wherein the throttling means comprises a plurality of throttling means having different throttling characteristics.

4. The device of claim 3, wherein the each of the plurality of throttling means is a different color.

5. The device of claim 1, wherein the throttling means comprises a selectively adjustable resistance to the flow of air.

6. The device of claim 1, wherein the throttling means impedes the outflow of the gaseous substance from the casing through the duct.

7. The device of claim 1, wherein the throttling means impedes the inflow of the gaseous substance towards the casing through the duct.

8. The device of claim 1, wherein the throttling means comprise a diaphragm having at least one air flow orifice with selectively calibrated dimensions.

9. The device of claim 8, wherein the diaphragm comprises a valve alternately forced into an opening position and a closing position by the flow of the gaseous substance through the duct in one and the other direction of flow respectively.

10. An arrangement for use in a ventricular assistance device comprising:
    a bag selectively adapted for at least first expanding to permit the filling of the bag with at least some of a body of blood flowing towards the bag;
    the bag selectively adapted for at least second contracting to expel from the bag at least some of the body of blood which has flowed into the bag;
    a containing casing enclosing the bag;
    a duct leading to the containing casing, the duct permitting the inflow and outflow of a gaseous substance to and from the containing casing following the expansion and contraction of the bag;
    means for selectively varying the resistance offered by the bag to filling with at least some of the body of blood; and
    throttling means acting selectively on the duct in at least one direction of flow.

11. The arrangement of claim 10, wherein the throttling means is removably coupled to the duct.

12. The arrangement of claim 10, wherein the throttling means comprises a plurality of throttling means having different throttling characteristics.

13. The arrangement of claim 12, wherein each of the plurality of throttling means is a different color.

14. The arrangement of claim 10, wherein the throttling means impedes the outflow of the gaseous substance from the containing casing through the duct.

15. The arrangement of claim 10, wherein the throttling means is coupled to the duct in order to impede the inflow of the gaseous substance through the duct to the containing casing.

16. The arrangement of claim 10, wherein the throttling means comprises a diaphragm provided with at least one air flow orifice having selectively calibrated dimensions.

17. The arrangement of claim 16, wherein the diaphragm comprises a valve alternately forced into an opening position and a closing position by the flow of the gaseous substance through the duct in one and the other direction of flow respectively.

18. A method for controlling the operation of a cardiac ventricular assistance device, comprising:
    selectively at least first expanding a bag enclosed in a containing casing to permit the filling of the bag with at least some of a body of blood flowing towards the bag;
    selectively at least second contracting the bag to expel from the bag at least some of the body of blood which has flowed into the bag;
    permitting the inflow and outflow of a gaseous substance through a duct and to and from the containing casing following the expansion and contraction of the bag;
    selectively varying the resistance offered by the bag to filling with at least some of the body of blood; and
    selectively throttling the duct in at least one direction of flow.

19. A method for controlling the operation of a cardiac ventricular assistance device, comprising:
    first expanding a bag enclosed in a casing to permit the filling of the bag with at least some of a body of blood flowing towards the bag;
    second contracting the bag to expel from the bag at least some of the body of blood which has flowed into the bag;
    selectively throttling a duct in at least one of a inflow and outflow direction;
    permitting in an essentially unimpeded way flow of said gaseous substance in the other of said inflow and outflow directions; and
    permitting the inflow and outflow of a gaseous substance to and from the containing casing following the expansion and contraction of the bag.

* * * * *